United States Patent [19]

Mooradian

[11] 4,224,335
[45] Sep. 23, 1980

[54] TETRAHYDROCARBAZOLES AND THEIR USE

[75] Inventor: Aram Mooradian, Schodack, N.Y.

[73] Assignee: Sterling Drug Inc., New York, N.Y.

[21] Appl. No.: 651,882

[22] Filed: Jan. 23, 1976

Related U.S. Application Data

[63] Continuation-in-part of Ser. No. 465,238, Apr. 29, 1974, abandoned, which is a continuation-in-part of Ser. No. 425,205, Dec. 17, 1973, Pat. No. 3,959,309, which is a continuation-in-part of Ser. No. 172,206, Aug. 16, 1971, abandoned, which is a continuation-in-part of Ser. No. 793,545, Jan. 23, 1969, abandoned, which is a continuation-in-part of Ser. No. 659,606, Aug. 10, 1967, Pat. No. 3,642,816.

[51] Int. Cl.² ............................................. A61K 31/40
[52] U.S. Cl. .................................................. 424/274
[58] Field of Search ........................ 260/315; 424/274

[56] References Cited

U.S. PATENT DOCUMENTS

| | | | |
|---|---|---|---|
| 3,592,824 | 7/1971 | Schut | 260/315 |
| 3,642,816 | 2/1972 | Mooradian | 260/315 |
| 3,752,823 | 8/1973 | McManus | 260/315 |
| 3,769,298 | 10/1973 | McManus | 260/315 |

FOREIGN PATENT DOCUMENTS 1386391  3/1975  United Kingdom ..................... 260/315

*Primary Examiner*—Frederick E. Waddell
*Attorney, Agent, or Firm*—Frederik W. Stonner; B. Woodrow Wyatt

[57] ABSTRACT

There are disclosed novel 3-amino(and substituted amino)-hydroxy (and dihydroxy)-1,2,3,4-tetrahydrocarbazoles having positive inotropic activity and methods and compositions for the use thereof in treating the failing heart in mammals afflicted with congestive heart failure.

9 Claims, No Drawings

TETRAHYDROCARBAZOLES AND THEIR USE

This application is a continuation-in-part of copending application Ser. No. 465,238, filed Apr. 29, 1974, now abandoned, in turn a continuation-in-part of application Ser. No. 425,205, filed Dec. 17, 1973, now U.S. Pat. No. 3,959,309, issued May 25, 1976 (of which pending application Ser. No. 579,157, filed May 20, 1975, now U.S. Pat. No. 4,062,864, also is a continuation-in-part), in turn a continuation-in-part of application Ser. No. 172,206, filed Aug. 16, 1971, now abandoned, in turn a continuation-in-part of application Ser. No. 793,545, filed Jan. 23, 1969, now abandoned, in turn a continuation-in-part of application Ser. No. 659,606, filed Aug. 10, 1967, now U.S. Pat. No. 3,642,816, issued Feb. 15, 1972.

The invention provides a method of treating the failing heart in mammals afflicted with congestive heart failure.

This invention further provides novel tetrahydrocarbazoles and pharmaceutical compositions suitable for treating the failing heart in mammals afflicted with congestive heart failure.

Congestive heart failure in mammals results from heart disease or other causes, for example, hypertension, valvular affection, arteriosclerosis, etc. In the treatment of the failing heart in mammals afflicted with congestive heart failure, a cardiotonic drug is administered. Such a drug stimulates the cardiac muscle to greater contractile force, i.e., provides a positive inotropic effect, thus restoring essentially normal tonicity of the congestive heart. The mammal afflicted with congestive heart failure must be maintained on cardiotonic drug therapy at dose levels of the drug which are effective to continually provide a positive inotropic effect. A well known class of drugs having cardiotonic activity which are commonly used in the treatment of congestive heart failure are the cardiac glycosides of the digitalis type.

In a method aspect of this invention there is provided a method for treating the failing heart in mammals afflicted with congestive heart failure which comprises administering to said mammal a 3-A-9-R-$Q_1$-$Q_2$-1,2,3,4-tetrahydrocarbazole having in the free base form the structural formula

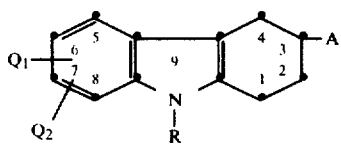

I where
- $Q_1$ is 7-hydroxy, $Q_2$ and R each are hydrogen, and A is amino or 1-pyrrolidyl; or
- $Q_1$ is 6-hydroxy, $Q_2$ is hydrogen or 7-fluoro, R is hydrogen, and A is dimethylamino; or
- $Q_1$ is 5-hydroxy or 7-hydroxy, $Q_2$ is hydrogen, R is methyl, and A is dimethylamino; or
- $Q_1$ is 6-hydroxy, $Q_2$ is 7-hydroxy, R is hydrogen, and A is amino, ethylamino or dimethylamino;

and pharmaceutically acceptable acid-addition salts thereof, in an amount effective to provide a positive inotropic effect.

In a first compound aspect of the invention there is provided a compound selected from 3-(dimethylamino)-6-hydroxy-1,2,3,4-tetrahydrocarbazole, 3-(dimethylamino)-7-fluoro-6-hydroxy-1,2,3,4-tetrahydrocarbazole, 3-(dimethylamino)-5-hydroxy-9-methyl-1,2,3,4-tetrahydrocarbazole, 3-(dimethylamino)-7-hydroxy-9-methyl-1,2,3,4-tetrahydrocarbazole, 3-(1-pyrrolidyl)-7-hydroxy-1,2,3,4-tetrahydrocarbazole, and 3-amino-7-hydroxy-1,2,3,4-tetrahydrocarbazole; and acid-addition salts thereof.

In a second compound aspect of the invention there is provided a compound selected from 3-amino-6,7-dihydroxy-1,2,3,4-tetrahydrocarbazole, 3-(ethylamino)-6,7-dihydroxy-1,2,3,4-tetrahydrocarbazole and 3-(dimethylamino)-6,7-dihydroxy-1,2,3,4-tetrahydrocarbazole; and acid-addition salts thereof.

By virtue of possessing an asymmetric carbon atom, that is, the carbon atom at the 3-position of the 1,2,3,4-tetrahydrocarbazole ring, each of the compounds of formula I can exist as optical isomers, that is, in two stereoisomeric forms (enantiomers), whose molecular structures are mirror images of each other. Therefore, within the purview of this invention are the dextrorotatory isomers and levorotatory isomers, hereinafter the d- and l-isomers, and the d,l-mixtures thereof, hereinafter racemic mixtures, of the compounds of formula I. The racemic mixture of any particular compound of formula I, obtained directly by the synthetic procedures described hereinbelow, is separated into the d-isomer and l-isomer, using standard resolution procedures. Thus the racemic mixture is converted to a mixture of two diastereomeric acid-addition salts by reaction, using standard procedures, with a suitable optically active acid, e.g., d-tartaric acid, l-malic acid, l-mandelic acid, d-camphor-10-sulfonic acid, dibenzoyl l-tartaric acid and the like and the resulting two diastereomeric salts in the mixture, which are no longer identical or mirror images and therefore possess different physical properties, are separated by conventional physical procedures such as crystallization. The two separated diastereomeric salts so obtained can then be converted by standard procedures, e.g., by treatment with base, to the corresponding d-isomer and l-isomer.

The compounds of formula I are useful both in the free base form and in the form of acid-addition salts, and both forms are within the purview of the invention. The acid-addition salts are simply a more convenient form for use, and in practice, use of the salt form inherently amounts to use of the base form. When the compounds of the invention represented by formula I are to be utilized for pharmaceutical purposes, the acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Appropriate medicinally acceptable salts within the scope of the invention are those derived from mineral acids such as hydrochloric acid, hydrobromic acid, hydriodic acid, nitric acid, phosphoric acid, sulfamic acid and sulfuric acid; and, organic acids such as cyclohexanesulfamic acid, methanesulfonic acid, ethanesulfonic acid, benzenesulfonic acid, p-toluenesulfonic acid, naponic acid (1,4-naphthalenedisulfonic acid), quinic acid, and the like, giving the hydrochloride, hydrobromide, hydroiodide, nitrate, phosphate, sulfamate, sulfate, cyclohexanesulfamate, methanesulfonate, ethanesulfonate, benzenesulfonate, p-toluenesulfonate, naponate and quinate respectively.

The acid-addition salts of the bases of formula I are obtained by dissolving either or both of the base and the acid separately in water or an organic solvent and mixing the two solutions or by dissolving both the base and the acid together in water or an organic solvent. The resulting acid-addition salt is isolated by filtration if it is insoluble in the reaction medium or by concentration of the solution or dilution of the solution with a solvent in which the acid-addition salt is insoluble or only sparingly soluble, or by evaporation of the reaction medium to leave the acid-addition salt as a residue.

Although medicinally acceptable salts of basic compounds I are used for pharmaceutical purposes, all acid-addition salts thereof are within the scope of the product aspects of the invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The compounds of formula I, when tested in one or more of the standard biological test procedures more fully described hereinbelow, were found to possess useful cardiotonic activity, i.e., positive inotropic activity, thus indicating their utility as cardiotonic agents in the treatment of congestive heart failure. The efficacy of these compounds was judged, in vitro, on the basis of percent increase in contractile force in isolated cat atria and papillary muscle and/or, in vivo, on the basis of percent increase in cardiac contractile force in the intact anesthetized dog.

The in vitro test procedures used are described as follows:

Cardiotonic Test Procedure I

Male cats weighting from 0.8 to 1.5 kg. were anesthetized with α-chloralose (80 mg./kg. i.p.). The chest was opened, the heart excised and the two atria dissected. A silk suture was tied to each of two opposite sides of the right atrium. One side of the atrium was tied to a glass rod and then mounted in a 50 ml. organ bath filled with Tyrode's solution. The second suture was attached to a force displacement transducer and the tension on the atrium was adjusted to 1.5±0.5 grams. The transducer was then connected to a Grass polygraph and the force and rate of atrial contraction was recorded continuously. The left atrium was treated similarly using silver wire instead of silk sutures. The silver wire also served as a stimulating electrode. Both atria were mounted in the same bath. The right atrium was beating spontaneously due to the presence of the sinoatrial node, while the left atrium was stimulated electrically at a rate of 3 beats/sec. by suprathreshold rectangular pulses of 5 millisecond duration. The Tyrode's solution bathing the atria was of the following composition (in mM): NaCl 136.87, KCl 5.36, NaH$_2$PO$_4$ 0.41, CaCl$_2$ 1.80, MgCl$_2$6H$_2$O 1.05, NaHCO$_3$ 11.90, glucose 5.55 and EDTA 0.04. The solution was equilibrated with a gas mixture consisting of 95% O$_2$ and 5% CO$_2$. The preparation was left to equilibrate for one hour before any drug was added. The bathing fluid was changed 3 to 4 times during the equilibration time. At the end of equilibration period, the drug dissolved in a vehicle or the vehicle alone was added to the tissue bath and the full response recorded. The vehicle used was Tyrode's solution to which, if required, sufficient acid was added to cause solution of the drug. When the response reached a maximum it was abolished by 3 washes at 10 min. intervals or until pre-drug values of force of contraction were reached. Generally, a dose response study of at least 3 doses was done in the same preparation.

Cardiotonic Test Procedure IB

Male cats 0.8 to 1.5 kg. were anesthetized with α-chloralose (80 mg./kg. i.p.). The chest was opened and the heart excised. The heart was dipped and shaken in Tyrode's solution for the removal of blood from the cavities. The right ventricle was then slit open and the small and thin (about 1 mm. in diameter and 4 to 7 mm. in length) papillary muscles were dissected out. A silver wire was attached to each of the two ends of the papillary muscle. The ventricular end was attached to a platinum electrode and mounted in a tissue bath containing Tyrode's solution described above. The silver wire on the valvular end of the muscle was attached to a force displacement transducer for the measurement of the force and rate of muscle contraction. The muscle was stimulated at a rate of 3 beats/sec. by suprathreshold rectangular pulses of 5 millisecond duration. The rest of the procedure was continued as described above.

Cardiotonic Test Procedure II

The in vivo test procedure used is described as follows: Mongrel dogs of both sexes and varying in weight from 9 to 15 kg. were anesthetized with 30 mg./kg. pentobarbital sodium administered intravenously. The trachea was exposed and cannulated. The tracheal cannula was then attached to a Harvard respiratory pump using room air. The right femoral artery and vein were cannulated. The arterial cannula was attached to a Statham P23A pressure transducer connected to a Grass polygraph for the continuous recording of arterial blood pressure. The venous cannula was used for the intravenous administration of drugs. Pin electrodes were attached to the right forelimb and left hindlimb. The electrodes were then connected to a Grass polygraph for the continuous recording of the standard limb lead II electrocardiogram. A ventro-dorsal incision at the third inter-costal space was made, the ribs laterally retracted and the pericardium slit open to expose the myocardium. The base of the aorta was dissected and a flow probe was fitted around it. The flow probe was attached to a square wave electromagnetic flowmeter (Carolina Medical Electronics). The flowmeter was then connected to a Grass polygraph for the continuous recording of aortic blood flow. This flow was used as an index of cardiac output (actual cardiac output is aortic blood flow+coronary blood flow). Cardiac contractile force was measured by suturing a Walton-Brodie strain gauge to the wall of the right ventricle. At the end of the surgical procedure, the animal was left to rest and equilibrate for one hour with continuous recording of blood pressure, EKG, cardiac contractile force and aortic blood flow. After the equilibration period, the vehicle or the drug dissolved in the vehicle was administered by intravenous infusion (i.v. inf.), intravenous bolus (i.v. bol.) or intraduodenally (i.d.) and the response of all the parameters measured to drug administration was recorded continuously for different periods of times depending on the route of drug administration. When the route of administration was i.v. inf., the drug was administered until a peak effect was reached and infusion was then maintained for ten minutes. The above-described test systems were standardized using dopamine.

By way of illustration the compounds of Examples 4C, 8 and 9F described hereinbelow, when tested in vitro in the cardiotonic test procedures IA and IB described hereinbefore, were effective in producing a significant percent increase (at least 30%) from controls in right atrial and/or papillary muscle force in the dose range of from 30 µg/cc to 100 µg/cc. Results obtained in test procedures IA and IB for compounds of formula I, identified by their example numbers (Ex.), are given in Table I where the percent changes from control in right atrial rate, right atrial force and papillary muscle force (positive unless otherwise indicated) is listed under RAR, RAF and PMF respectively, and C is the concentration in µg/cc at which the compound was tested. The concentration for each compound was calculated on the basis of the free base. The percent change given for each compound is the average of values obtained in from two to six tests for a particular dose.

TABLE I

|  | C | RAR | RAF | PMF |
|---|---|---|---|---|
| Ex. 4C$^{(a)}$ | 30 | 0 | 13 | 59 |
|  | 100 | 12 | 39 | 116 |
| Ex. 8 | 30 | 31 | 25 | 55 |
| Ex. 9F$^{(b)}$ | 10 | 4 | 13 | 43 |
|  | 30 | 8 | 42 | 53 |
|  | 100 | 1 | 58 | 67 |

$^{(a)}$hydrochloride salt
$^{(b)}$methanesulfonate salt.

By way of illustration, the compounds of Examples 1, 2, 3, 4C, 5C, 6, 7C and 9F described hereinbelow, when tested in vivo in cardiotonic test procedure II, were effective in producing a significant percent increase (at least 30%) over controls in myocardial contractile force when administered by one or more of the following routes: i.v. infusion in a dose range of from 0.03 to 0.3 mg./kg. per minute; i.v. bolus in a dose range of from 1 to 10 mg./kg., and i.d. at 30 to 60 mg./kg. Results for compounds of formula I, identified by their example numbers (Ex.), are given in Table 2 in which positive (+) and negative (−) percent changes from control in myocardial contractile force, heart rate, systolic blood pressure and diastolic blood pressure are listed under CF, HR, SBP and DBP respectively, D is the dose in mg./kg. (per minute in the case of i.v. inf.) and Route is the route of administration. The dose for each compound was calculated on the basis of the free base. The percent changes given for each compound are an average of values obtained in from two to six dogs for a particular dose except as otherwise indicated. Where the duration of activity of a particular compound was determined, the average duration in minutes is listed in Table II under DUR.

TABLE II

|  | D | Route | CF | HR | SBP | DBP | DUR |
|---|---|---|---|---|---|---|---|
| Ex. 1$^{(a)}$ | 3 | i.v. bol. | +27 | −9 | +17 | +7 | <1 |
|  | 10 | i.v. bol. | +78 | +11 | 0 | −24 | 2 |
| Ex. 1$^{(b)}$ | 3 | i.v. bol. | +34 | 0 | +10 | +6 | 20 |
|  | 10 | i.v. bol. | +59 | −1 | −6 | −18 | 20 |
| Ex. 1$^{(a)}$ | 30 | i.d. | +40 | −10 | +17 | +16 | 60 |
| Ex. 2B | 1$^{(c)}$ | i.v. bol | +50 | −28 | −38 | −40 | 10 |
|  | 3$^{(c)}$ | i.v. bol | +65 | −29 | −41 | −45 | 5 |
| Ex. 3$^{(a)}$ | 0.30 | i.v. inf. | +59 | −14 | +28 | +6 |  |
| Ex. 4C$^{(a)}$ | 1 | i.v. bol. | +32 | +5 | +1 | 0 | 5 |
|  | 3 | i.v. bol. | +112 | +23 | −27 | −34 | 5 |
| Ex. 5C$^{(a)}$ | 0.30 | i.v. inf. | +59 | −4 | +2 | −6 |  |
| Ex. 6 | 0.03 | i.v. inf. | +77 | 0 | +4 | +2 | 60 |

TABLE II-continued

|  | D | Route | CF | HR | SBP | DBP | DUR |
|---|---|---|---|---|---|---|---|
|  | 0.10 | i.v. inf. | +120 | +17 | +47 | +47 | 82 |
| Ex. 7C | 0.03$^{(d)}$ | i.v. inf. | +49 | +18 | −9 | −8 | 23 |
|  | 0.10$^{(d)}$ | i.v. inf. | +163 | +28 | +94 | +65 | 48 |
| Ex. 9F$^{(b)}$ | 30 | i.d. | +43 | +9 | +5 | +8 | 42 |
|  | 60$^{(c)}$ | i.d. | +63 | −12 | −29 | −38 | 45 |
|  | 0.10$^{(c)}$ | i.v. inf. | +33 | +6 | −3 | −12 | 30 |
|  | 10$^{(c)}$ | i.v. bol. | +100 | −6 | −64 | −80 | 10 |

$^{(a)}$hydrochloride salt
$^{(b)}$methanesulfonate salt
$^{(c)}$values obtained in one dog
$^{(d)}$average of three values obtained in the same dog In utilizing the compounds of formula I for treating the failing heart in mammals afflicted with congestive heart failure, the dose to be administered and the frequency of administration will be dependent on the potency and duration of activity of the compound to be administered as well as on the route of administration.

While all the compounds of formula I are useful as cardiotonic agents for oral and intravenous administration, the longer the duration of positive inotropic effect of any particular compound, the more preferred is such a compound for use by oral administration.

On the basis of the test results obtained in the cardiotonic test procedure described hereinabove and the well known fact that the cardiac activity of a drug in intact dogs is correlated with identical cardiac activity in humans, the compounds of formula I are indicated for use in treating the failing heart in humans afflicted with congestive heart failure. Doses of the compounds of formula I contemplated for use in treating the failing heart in congestive heart failure are about 0.03 mg. or greater per minute per person for intravenous infusion, about 1 mg. or greater per person for intravenous bolus, and about 30 mg. or greater per person orally.

The actual determination of the numerical biological data definitive for a particular compound is readily determined by technicians versed in pharmacological test procedures, without the need for any extensive experimentation.

The compositions of this invention can be administered orally in the form of pills, tablets, capsules, e.g., in admixture with talc, starch, milk sugar or other inert, i.e., non-toxic or pharmacologically acceptable pharmaceutical carrier, or in the form of aqueous solutions, suspensions, encapsulated suspension, gels, elixirs, aqueous alcoholic solutions, e.g., in admixture with sugar or other sweetening agents, flavorings, colorants, thickeners and other conventional pharmaceutical excipients. When injected subcutaneously, intramuscularly or intravenously, they can be administered, e.g., as an aqueous or peanut oil solution or suspension using excipients and carriers conventional for this mode of administration. The best route of administration and the best dosage will be apparent from the laboratory tests for activity and toxicity of the selected compound conventionally undertaken as part of the development phase of a pharmaceutical.

The molecular structures of the compounds of the invention were assigned on the basis of the method of their preparation and study of their NMR and/or IR spectra, and confirmed by the correspondence between calculated and found values for the elemental analyses of representative examples.

The invention is illustrated by the following examples without, however, being limited thereto.

EXAMPLE 1

To a solution of 20 g. of 3-(dimethylamino)-6-(benzyloxy)-1,2,3,4-tetrahydrocarbazole in ethyl alcohol was added 2 g. of 10% palladium-on-charcoal and the mixture was subjected to a hydrogen atmosphere at about 50 psig for about one hour. The catalyst was removed by filtration, the filtrate was evaporated to dryness under reduced pressure, and the solid residue was recrystallized from ethyl acetate to give 7.4 g. of 3-(dimethylamino)-6-hydroxy-1,2,3,4-tetrahydrocarbazole, m.p. 202.4°–204.0° C. The hydrochloride salt, m.p. 281°–284° C., was obtained by hydrogenation of 3-(dimethylamino)-6-(benzyloxy)-1,2,3,4-tetrahydrocarbazole hydrochloride using a procedure similar to the foregoing. The methanesulfonate salt, m.p. 198°–201° C., was obtained by treating a solution of the free base in acetone with an equivalent of methanesulfonic acid, collecting the precipitate and triturating this with acetone and ether.

The preparation of 3-(dimethylamino)-6-(benzyloxy)-1,2,3,4-tetrahydrocarbazole is described in U.S. Pat. No. 3,642,816, issued Feb. 15, 1972.

EXAMPLE 2

(A) A solution of 1-methyl-1-(3-benzyloxyphenyl)-hydrazine hydrochloride (31.0 g.), prepared in a conventional manner from N-methyl-3-benzyloxyaniline by nitrosation and reduction with lithium aluminum hydride, and 4-dimethylaminocyclohexanone hydrochloride (21.5 g.) in 200 ml. of absolute ethyl alcohol was heated at reflux for forty-five minutes. The mixture was chilled and filtered and the collected solid was washed with 100 ml. of ethyl alcohol-water (1:1) and triturated with 100 ml. of water and filtered to give 33.5 g. of solid material. The aqueous ethyl alcohol reaction mother liquors were evaporated to dryness to give 13 g. of an oil. The material (33 g.) was slurried in 200 ml. of hot ethyl alcohol and the slurry was cooled and filtered. Slurrying was repeated in 500 ml. of ethyl alcohol and the resulting solid was dried to give 25 g. of 3-(dimethylamino)-7-(benzyloxy)-9-methyl-1,2,3,4-tetrahydrocarbazole hydrochloride, m.p. 280° C. The filtrate from 500 ml. ethyl alcohol slurry, on chilling, deposited 3.1 g. of 3-(dimethylamino)-5-(benzyloxy)-9-methyl-1,2,3,4-tetrahydrocarbazole hydrochloride, m.p. 198°–201° C.

(B) To a solution of 4.0 g. of 3-(dimethylamino)-5-(benzyloxy)-9-methyl-1,2,3,4-tetrahydrocarbazole hydrochloride in 150 ml. of ethyl alcohol was added 0.5 g. of 10% palladium-on-charcoal and the mixture was subjected to a hydrogen atmosphere at about 40 psig for six hours. The mixture was filtered, the filtrate was evaporated to dryness, the residue was triturated in ether and the solids obtained were recrystallized from ethyl alcohol to give 1.4 g. of 3-(dimethylamino)-5-hydroxy-9-methyl-1,2,3,4-tetrahydrocarbazole hydrochloride, m.p. 255°–258° C. (dec.).

EXAMPLE 3

3-(Dimethylamino)-7-hydroxy-9-methyl-1,2,3,4-tetrahydrocarbazole hydrochloride (4.2 g.), m.p. 295° C. (dec.) (methanesulfonate salt, m.p. 227°–230° C.), was obtained from 3-(dimethylamino)-7-(benzyloxy)-9-methyl-1,2,3,4-tetrahydrocarbazole hydrochloride (18 g.) (from Example 2A) following a procedure similar to that described in Example 2B.

EXAMPLE 4

(A) To a stirred slurry of 3,4-isopropylidenedioxyaniline hydrochloride (19.5 g.) in 80 ml. of concentrated hydrochloric acid and 15 ml. of water, cooled to −20° C., was added dropwise sodium nitrite (6.9 g.) in 70 ml. of water during one-half hour. Stirring was continued one-half hour and a solution of stannous chloride dihydrate (67.5 g.) in 70 ml. of water, cooled to −20° C., was added. The resulting dark precipitate was collected and dissolved in water. The aqueous solution was basified and extracted with ether and the ether extract was washed with saturated salt solution, dried and evaporated to dryness to yield 7.3 g. of oily 3,4-isopropylidenedioxyphenylhydrazine.

(B) 4-(Dimethylamino)-cyclohexanone hydrochloride (7.2 g.) and 3,4-isopropylidenedioxyphenylhydrazine (7.3 g.) were dissolved in 20 ml. of glacial acetic acid and the solution was allowed to stand for eighteen hours at room temperature. Water-ice (50 ml.) was added, the mixture was extracted with ether and the aqueous solution was basified and extracted with ether. The second ether extract was dried and evaporated to dryness and isopropyl alcohol was added to the resulting oil. The resulting precipitate was collected by filtration and dried to give 3.6 g. of 3-(di-methylamino)-6,7-isopropylidenedioxy-1,2,3,4-tetrahydrocarbazole, m.p. 184°–186° C. Concentration of the filtrate yielded 1.6 g. of material which was recrystallized from isopropyl alcohol to give 1 g. of additional product, m.p. 183°–185° C.

(C) 3-(Dimethylamino)-6,7-isopropylidenedioxy-1,2,3,4-tetrahydrocarbazole (6.9 g.) was slurried in 69 ml. of dioxane, 69 ml. of concentrated hydrochloric acid was added and the mixture was heated at 50° C. for ten minutes, cooled to room temperature and evaporated to dryness under reduced pressure with cautious external warming. Warm methyl alcohol was added to the residue and the resulting crystals were collected and recrystallized from methyl alcohol to give 6.5 g. of 3-(dimethylamino)-6,7-dihydroxy-1,2,3,4-tetrahydrocarbazole hydrochloride, m.p. 267°–270° C.; hydrobromide, m.p. 278°–280° C.

EXAMPLE 5

(A) To 3,4-Isopropylidenedioxyphenylhydrazine (19.5 g.) in 81 ml. of 2 N ethanolic hydrogen chloride and 100 ml. of absolute ethyl alcohol at room temperature was added 4-acetamidocyclohexanone (28 g.) with cooling to maintain the temperature below 35° C. The solution was kept at room temperature for sixteen hours, diluted with water and extracted with chloroform. The chloroform extract was evaporated to dryness under reduced pressure and the resulting residue was crystallized from benzene to give 27.2 g. of 3-acetamido-6,7-isopropylidenedioxy-1,2,3,4-tetrahydrocarbazole, m.p. 165°–167° C.

(B) To a solution of lithium aluminum hydride (3.1 g.) in 200 ml. of tetrahydrofuran was added 3-acetamido-6,7-isopropylidenedioxy-1,2,3,4-tetrahydrocarbazole (12 g.) and the solution was heated at reflux for eight hours and cooled. Water was added cautiously and the organic layer was separated and evaporated to dryness under reduced pressure. The resulting residue was triturated in ether to give, on filtration, 8.0 g. of 3-(ethylamino)-6,7-isopropylidenedioxy-1,2,3,4-tetrahydrocarbazole, m.p. 167°–169° C.

(C) 3-(Ethylamino)-6,7-isopropylidenedioxy-1,2,3,4-tetrahydrocarbazole (8 g.) in 75 ml. of concentrated hydrochloric acid was heated at reflux for three hours, and allowed to stand at room temperature for sixteen hours. The precipitate was filtered and recrystallized from water to give 5.7 g. of 3-(ethylamino)-6,7-dihydroxy-1,2,3,4-tetrahydrocarbazole hydrochloride, m.p. 243°–245° C.; hydrobromide, m.p. 286°–287° C.

EXAMPLE 6

3-Acetamido-6,7-isopropylidenedioxy-1,2,3,4-tetrahydrocarbazole (7 g.) in 70 ml. of concentrated hydrochloric acid was heated at reflux for four hours and evaporated to dryness. Ethyl alcohol was added and the resulting solids were collected and recrystallized from isopropyl alcohol-methyl alcohol to give 5.2 g. of 3-amino-6,7-dihydroxy-1,2,3,4-tetrahydrocarbazole hydrochloride, m.p. 279°–281° C.

EXAMPLE 7

(A) 3-Benzyloxyphenylhydrazine (46.5 g.), prepared from 3-benzyloxyaniline by a procedure similar to that described in Example 9D, and 4-acetamidocyclohexanone (27.9 g.) in 100 ml. of 2-N ethanolic hydrogen chloride and 150 ml. of absolute ethyl alcohol was heated on a steam bath for one-half hour. The mixture was cooled and the solids were collected and washed with isopropyl alcohol and water to give 28.8 g. of 3-acetamido-7-(benzyloxy)-1,2,3,4-tetrahydrocarbazole, m.p. 208°–209° C. (ethyl alcohol).

(B) 3-Acetamido-7-(benzyloxy)-1,2,3,4-tetrahydrocarbazole (16 g.) was hydrogenated in 200 ml. of ethyl alcohol containing 6 ml. of concentrated hydrochloric acid and 3 g. of 10% palladium on charcoal at 40 psig following a procedure similar to that described in Example 2B to yield 3-acetamido-7-hydroxy-1,2,3,4-tetrahydrocarbazole as a foam.

(C) The 3-acetamido-7-hydroxy-1,2,3,4-tetrahydrocarbazole above was heated in 150 ml. concentrated hydrochloric acid on a steam bath for fifty-five hours. The solution was concentrated and cooled and the resulting solid material was collected and recrystallized from 1:1 methyl alcohol-isopropyl alcohol to give 1.2 g. of 3-amino-7-hydroxy-1,2,3,4-tetrahydrocarbazole hydrochloride, m.p. 302°–303° C.

EXAMPLE 8

(A) Following a procedure similar to that described in Example 2A and using 4-(1-pyrrolidyl)-cyclohexanone (14.5 g.), 3-benzyloxyphenylhydrazine hydrochloride (21.8 g.), 160 ml. of absolute ethyl alcohol and 60 ml. of 4.5N ethanolic hydrogen chloride there was obtained 3-(1-pyrrolidinyl)-7-benzyloxy-1,2,3,4-tetrahydrocarbazole hydrochloride, 4 g. of which was hydrogenated, following a procedure similar to that described in Example 1C to give 1.3 g. of 3-(1-pyrrolidyl)-7-hydroxy-1,2,3,4-tetrahydrocarbazole hydrochloride, m.p. 294°–295° C. (methyl alcohol-water).

EXAMPLE 9

(A) 57% Sodium hydride (33.7 g.) was dissolved in one liter of dimethyl sulfoxide at 70° C. When a clear solution resulted there was added slowly, with stirring, aldoxime (97.4 g.) and to the resulting pasty mixture was added slowly, with vigorous stirring, 3,4-difluoronitrobenzene (63.6 g.) and stirring was continued two hours at 35°–40° C. The reaction mixture was poured into ice water containing 80 ml. concentrated hydrochloric acid, extracted with ether and the ether solution was extracted with dilute sodium hydroxide. The alkaline extract was acidified, extracted with ether, and the ether was evaporated to give 44.5 g. of crystalline 3-fluoro-4-hydroxynitrobenzene.

(B) To a solution of the product (44.5 g.) from Example 9A in 500 ml. of dimethyl sulfoxide was added sodium methoxide (16.8 g.) followed by benzyl chloride (38.3 g.) and the solution was heated on a steam bath with stirring for two hours and poured into ice-cold dilute sodium hydroxide. The resulting crystals were collected, washed with water, filtered and dried on the filter pad to give 66 g. of 4-benzyloxy-3-fluoronitrobenzene.

(C) The product (66 g.) from Example 9B was stirred in 350 ml. of water, 650 ml. ethyl alcohol and 50 ml. of acetic acid with iron filings (150 g.) with heating on a steam bath for twenty-four hours. The reaction mixture was allowed to stand sixteen hours at room temperature and then made alkaline with sodium bicarbonate, filtered, and the filtrate was evaporated to dryness. The resulting residue was taken up in ether/water, the ether extract was treated with ethereal hydrogen chloride and the solids were collected to give 28 g. of 4-benzyloxy-3-fluoroaniline hydrochloride.

(D) The product (28 g.) from Example 9C was dissolved in hot water and the solution was cooled. To the resulting stirred suspension was added 100 ml. of concentrated hydrochloric acid with cooling to 0° to 10° C. followed by dropwise addition of an aqueous solution containing sodium nitrite (7.6 g.) and stirring was continued two hours. Two additional portions of an aqueous solution containing sodium nitrite (6.9 g.) were added successively followed after each addition by two hours and one hour stirring, respectively. Stannous chloride (7.5 g.) in concentrated hydrochloric acid was then added with stirring. The mixture was allowed to stand under refrigeration for sixteen hours, filtered, and the collected solids were taken up in two liters of boiling methyl alcohol. Cooling and concentration of this solution and collection of the resulting solids gave 26 g. of 4-benzyloxy-3-fluorophenylhydrazine hydrochloride.

(E) The product (26 g.) from Example 9D and 4-dimethylaminocyclohexanone hydrochloride (18 g.) in 250 ml. of 95% ethyl alcohol were heated on a steam bath for two hours. Cooling of the mixture and filtration, followed by washing of the collected solids with ethyl alcohol, water and ethyl alcohol, yielded 28 g. of 3-(dimethylamino)-6-(benzyloxy)-7-fluoro-1,2,3,4-tetrahydrocarbazole hydrochloride.

(F) To the product (20 g.) from Example 9E in 200 ml. of dimethyl sulfoxide was added 3 g. of 10% palladium on charcoal and the mixture was subjected to a hydrogen atmosphere at about 50 psig for two hours, filtered and the filtrate was concentrated to dryness under reduced pressure. The residue was slurried in isopropyl alcohol and the solids were collected and dissolved in 500 ml. of water. The aqueous solution was treated with excess ammonium hydroxide and the resulting solids were collected, dried and dissolved in 500 ml. of hot acetone. To the hot acetone solution was added methanesulfonic acid (4 g.) in acetone. The partly crystalline material was separated from the acetone by decantation and crystallized by treatment with acetone-isopropyl alcohol. The solids were collected, combined with additional material precipitated from the original acetone mother liquors by addition of ether, and recrystallized from methyl alcohol to give 8.7 g. of 3-(dimethylamino)-7-fluoro-6-hydroxy-1,2 3,4-tetrahydrocarbazole methanesulfonate, m.p. 207°–210° C.

I claim:

1. A method for treating the failing heart in a mammal afflicted with congestive heart failure which comprises administering intravenously or orally to said mammal a compound selected from the group consisting of 3-(dimethylamino)-6-hydroxy-1,2,3,4-tetrahydrocarbazole, 3-(dimethylamino)-7-fluoro-6-hydroxy-1,2,3,4-tetrahydrocarbazole, 3-(dimethylamino)-5-hydroxy-9-methyl-1,2,3,4-tetrahydrocarbazole, 3-(dimethylamino)-7-hydroxy-9-methyl-1,2,3,4-tetrahydrocarbazole, 3-(1-pyrrolidyl)-7-hydroxy-1,2,3,4-tetrahydrocarbazole and 3-amino-7-hydroxy-1,2,3,4-tetrahydrocarbazole; and pharmaceutically acceptable acid-addition salts thereof; in an amount effective to provide a positive inotropic effect.

2. A method according to claim 1 wherein the compound administered is selected from the group consisting of 3-(dimethylamino)-6-hydroxy-1,2,3,4-tetrahydrocarbazole, 3-(dimethylamino)-7-fluoro-6-hydroxy-1,2,3,4-tetrahydrocarbazole, 3-(dimethylamino)-5-hydroxy-9-methyl-1,2,3,4-tetrahydrocarbazole, 3-(dimethylamino)-7-hydroxy-9-methyl-1,2,3,4-tetrahydrocarbazole and 3-amino-7-hydroxy-1,2,3,4-tetrahydrocarbazole; and pharmaceutically acceptable acid-addition salts thereof.

3. A method according to claim 2 wherein the compound administered is selected from the group consisting of 3-(dimethylamino)-6-hydroxy-1,2,3,4-tetrahydrocarbazole, 3-(dimethylamino)-5-hydroxy-9methyl-1,2,3,4-tetrahydrocarbazole, 3-(dimethylamino)-7-hydroxy-9-methyl-1,2,3,4-tetrahydrocarbazole and 3-amino-7-hydroxy-1,2,3,4-tetrahydrocarbazole; and pharmaceutically acceptable acid-addition salts thereof.

4. A method according to claim 1 wherein 3-(1-pyrrolidyl)-7-hydroxy-1,2,3,4-tetrahydrocarbazole or a pharmaceutically acceptable acid-addition salt thereof is administered.

5. A method according to claim 2 wherein 3-(dimethylamino)-7fluoro-6-hydroxy-1,2,3,4-tetrahydrocarbazole or a pharmaceutically acceptable acid-addition salt thereof is administered.

6. A method according to claim 3 wherein 3-(dimethylamino)-6-hydroxy-1,2,3,4-tetrahydrocarbazole or a pharmaceutically acceptable acid-addition salt thereof is administered.

7. A method according to claim 3 wherein 3-amino-7-hydroxy-1,2,3,4-tetrahydrocarbazole or a pharmaceutically acceptable acid-addition salt thereof is administered.

8. A method for treating the failing heart in a mammal afflicted with congestive heart failure which comprises administering intravenously or orally to said mammal a compound selected from the group consisting of 3-amino-6,7-dihydroxy-1,2,3,4-tetrahydrocarbazole, 3-(ethylamino)-6,7-dihydroxy-1,2,3,4-tetrahydrocarbazole and 3-(dimethylamino)-6,7-dihydroxy-1,2,3,4-tetrahydrocarbazole; and pharmaceutically acceptable acid-addition salts thereof; in an amount effective to provide a positive inotropic effect.

9. A method according to claim 8 wherein 3-amino-6,7-dihydroxy-1,2,3,4-tetrahydrocarbazole or a pharmaceutically acceptable acid-addition salt thereof is administered.

* * * * *